United States Patent [19]

Miyasaka et al.

[11] Patent Number: 4,915,704
[45] Date of Patent: Apr. 10, 1990

[54] TUBE ASSEMBLY WITH A BREAKAWAY PLUG

[75] Inventors: Eiichi Miyasaka; Tetsuro Nishimura; Kazuhiko Sudo, all of Shizuoka, Japan

[73] Assignee: Terumo Kabushiki Kaisha, Tokyo, Japan

[21] Appl. No.: 212,216

[22] Filed: Jun. 27, 1988

[51] Int. Cl.⁴ .............................................. A61M 25/00
[52] U.S. Cl. .................................. 604/256; 604/284; 604/905
[58] Field of Search ............... 604/148, 256, 283, 284, 604/244, 905, 197, 263; 215/253, 277; 220/258, 276

[56] References Cited

U.S. PATENT DOCUMENTS 4,654,031  3/1987  Lentz ................................. 604/256
4,731,061  3/1988  Matkovich ......................... 604/256

Primary Examiner—Stephen C. Pellegrino
Attorney, Agent, or Firm—Burns, Doane, Swecker & Mathis

[57] ABSTRACT

An assembly of a tube having a breakaway plug mounted on one opening thereof is provided. The plug includes a hollow cylindrical segment fixedly secured to the tube, a closing segment, and a frangible thin-wall portion located in the hollow segment apart from the secured portion. A protector of a relatively rigid material is fitted over the plug. The plug can be torn off at the frangible portion by twisting the protector.

6 Claims, 5 Drawing Sheets

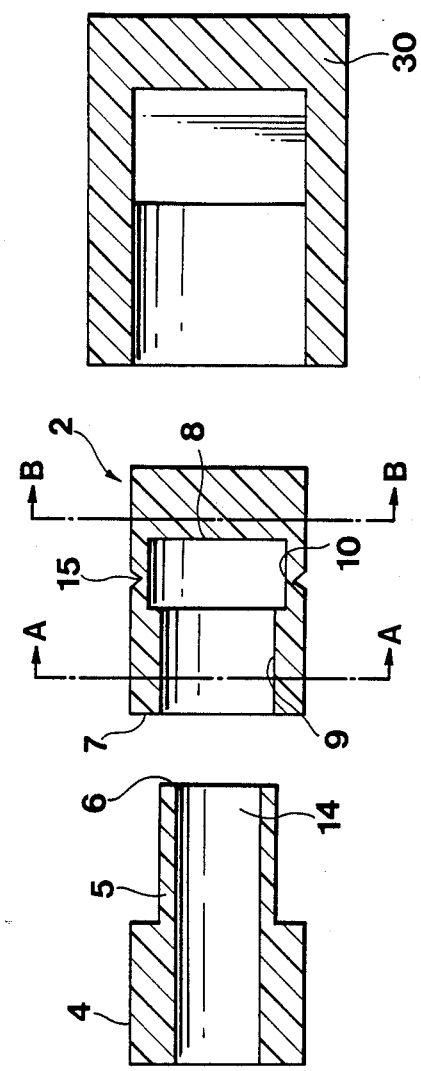
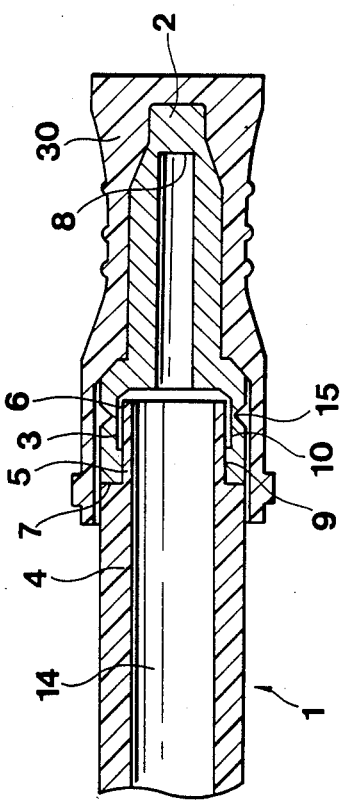

FIG. 5a
(PRIOR ART)
FIG. 5b
(PRIOR ART)
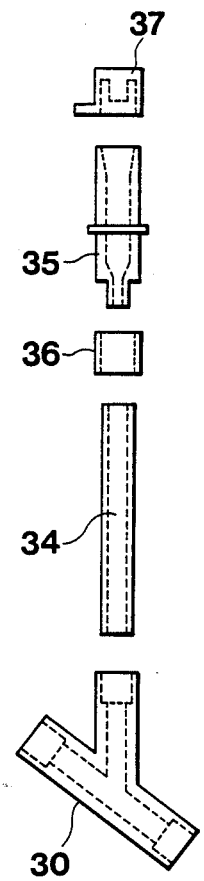
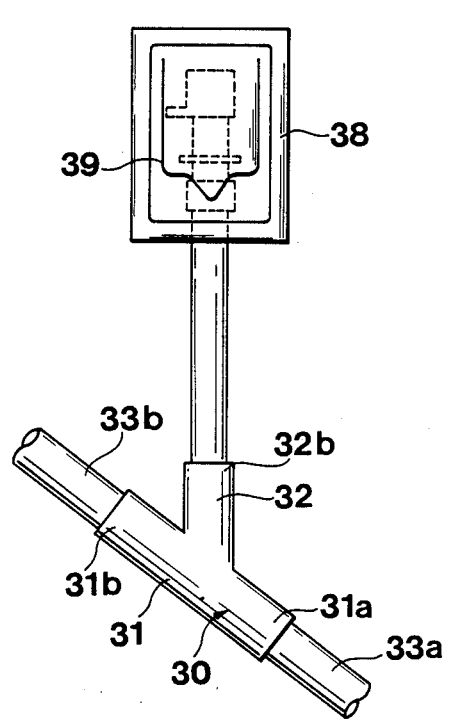

4,915,704

TUBE ASSEMBLY WITH A BREAKAWAY PLUG

BACKGROUND OF THE INVENTION

1. Field of the Invention

This invention relates to a tube assembly with a breakaway plug. More particularly, it relates to a tube assembly having a breakaway plug which is unlikely to be ruptured or contaminated before use.

2. Discussion of Prior Art

Referring to FIG. 5b, there is illustrated one prior art tube assembly. A Y-shaped branch tube 30 illustrated in FIG. 5b comprises a main tube 31 and a branch tube 32. The main tube 31 has two openings, that is, a proximal opening 31a to be connected to a venipuncture needle (not shown) for blood collection, and a distal opening 31b to be connected to a tubing 33b which is further connected to a blood bag (not shown). The branch tube 32 has a distal opening 32b which has a blood-returning assembly mounted thereon.

The component constituting the blood-returning assembly are shown together with the branch tube 30 in FIG. 5a in an exploded state. The blood returning assembly comprises a sleeve 34 mounted on the distal opening 32b, connector 35 fitted in the sleeve 34, caulking member 36 to fluid-tightly join the sleeve 34 and the connector 35, and a rubber cap 37 fitted on the connector 37. The blood returning assembly is enclosed in an envelope 38 for preventing contamination. The envelope 38 has a peeling line 39 for ease of opening the envelope 38.

Upon returning blood corpuscles, the envelope 38 is opened at the peeling line 39, and the cap 37 is then removed for connecting another member to the connector 35.

The blood returning assembly as described above has a plurality of drawbacks as described below.

(1) Since the blood returning assembly comprises a number of components, the number of joints are also increased resulting in an increased risk of contamination. Efficiency in course of assembly is also lowered.

(2) Since the medical solution in the blood bag directly contacts the rubber cap via tubings, amount of the substances eluted from the rubber cap is increased although the amount is below the standard value.

(3) The rubber cap may be loosened, or even come off in an extreme case, due to an increased inner pressure of the blood bag during an autoclave sterilization of the system.

(4) The blood returning assembly is wrapped with the envelope by way of precaution against the contamination in (3). Upon returning the blood corpuscles, a troublesome step of opening the envelope is required before taking the rubber cap off. Complicated operation increases the risk of contamination and lowers the operation efficiency.

SUMMARY OF THE INVENTION

An object of the present invention is to provide a tube assembly having a breakaway plug which is not likely to be accidentally ruptured or contaminated during manufacture or transportation, but can be readily torn off upon use.

According to the present invention, there is provided a tube assembly comprising a tubular body having at least two open ends, a plug of a relatively flexible material mounted on one open end of said tubular body, the plug including (a) a hollow mount segment having an open end, a portion of the mount segment extending from its open end being fixedly secured to the one open end of the tubular body, (b) a closing segment axially connected to the mount segment, and (c) a frangible portion located axially outside the secured portion whereby the plug is breakable at the frangible portion and removable from the one open end of the tubular body, and a protector of a relatively rigid material fitted over the plug.

In one preferred embodiment, the mount segment includes a first wall portion with a relatively smaller inner diameter extending from the open end of the mount segment and a second wall portion with a relatively larger inner diameter extending from the first wall portion to the closing segment. The first wall portion is secured to the one open end of the tubular body and the frangible portion is a circumferential notch in the outer surface of the second wall portion.

The protector is in close fit on the closing segment of the plug, but extends over the frangible portion with a spacing from the mount segment. The protector has such a hardness that it may not prevent breakage of the plug at the frangible portion.

The open end of the tubular body axially extends beyond the frangible portion of the plug toward the closing segment of the plug.

The closing segment of the plug has a non-circular cross section in a direction transvease to an axial direction.

BRIEF DESCRIPTION OF THE DRAWINGS

The above and other objects, features, and advantages of the invention will be better understood by reading the following description taken in conjunction with the accompanying drawings, in which:

FIG. 2a is an exploded cross-sectional view of the tube assembly of the present invention showing a tube branch, a plug and a protector in a disassembled state;

FIG. 2b is a cross-sectional view of the tube assembly showing a tube branch, a plug and a protector in an assembled state;

FIG. 5a is an exploded view of a prior art tube assembly; and

FIG. 5b is a front view of the prior art tube assembly in an assembled state.

DESCRIPTION OF THE PREFERRED EMBODIMENT

The tube assembly of the present invention includes a tube body having at least two open ends. Any tubular body having at least two open ends between which a flow path extends may be employed. Although a commonly used four-way branch tube is referred to as a typical example in the following description, the present invention is not limited to the four-way branch tube.

Figure 1:
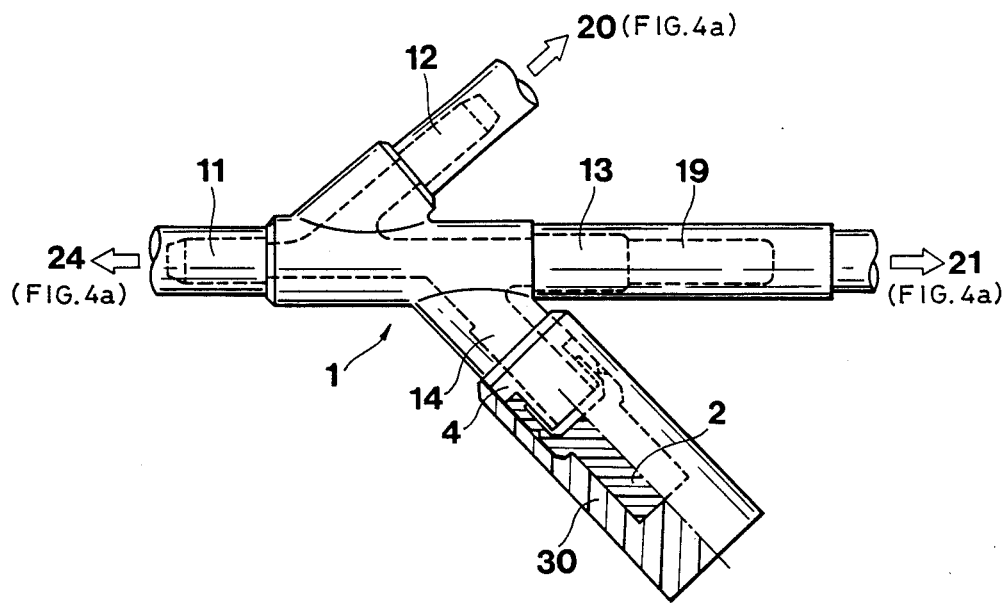
FIG. 1 is a partially cross-sectional plane view of a tube assembly with a breakaway plug according to one embodiment of the present invention.

FIG. 1 illustrates a four-way branch tube as one embodiment of the tube assembly of the present invention.

Figure 4A:
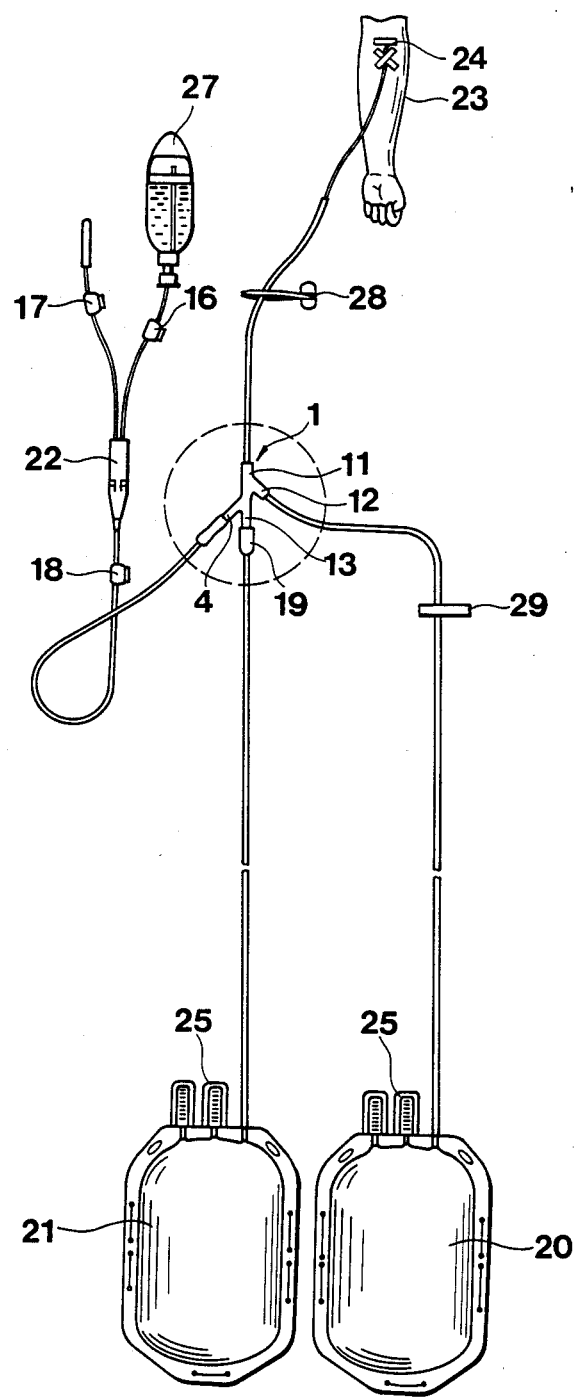
FIG. 4a and 4b illustrate a plasmapheresis system having the tube assembly of the invention incorporated therein.

It will be understood that FIG. 1 is an enlarged view corresponding to a circled portion in the system of FIG. 4a. The four-way branch tube illustrated in FIG. 1 has four openings, that is, a first opening 11 to be connected to a puncture needle 24 for blood collection, a second opening 12 to be connected to a first blood bag 20, a third opening 13 to be connected to a second blood bag 21, and a fourth opening 14 having a plug 2 mounted thereon (see FIG. 4a). For brevity of description, a flow path communicating between the first and second openings 11 and 13 is designated a main flow path. With respect to the main flow path, the first opening 11 to be connected to the needle 24 is designated a proximal end and the second, third and fourth openings 12, 13 and 14 are designated distal ends.

The feature of the present invention resides in a combination of the branch 4 having the fourth opening 14, the plug 2 mounted on the branch 4, and a protector 30 mounted on the plug. The components are described in detail in FIG. 2a which is a cross-sectional view of the branch 4, the plug 2, and the protector 30 in an exploded state. A full assembly of these components is shown in FIG. 2b although the illustrated components are modified ones.

The branch 4 of the four-way branch tube has a flow path-defining bore 14 terminating at an open end 6 and includes a stepped wall portion 5 having a smaller outside diameter than the remaining. The outside wall of the branch is stepped to form the smaller outside diameter wall portion 5 for mounting the plug 2 thereon.

The plug 2 includes a hollow mount segment providing an open end 7 at one end and a closing segment axially connected to the mount segment and providing a closing end 8 at another end. The hollow mount segment includes a first wall portion 9 with a relatively smaller inner diameter extending a predetermined distance from the open end 7 and a second wall portion 10 with a relatively larger inner diameter extending from the first wall portion 9 to the closing segment. The first wall portion 9 is fixedly secured to the stepped wall portion 5 of the branch 4 as shown in FIG. 2b. The second wall portion 10 is provided with a frangible portion in the form of a circumferential notch 15 in the outer surface whereby the plug is breakable at the frangible portion and removable from the branch. The closing segment may be either a solid segment as shown in FIG. 2a or a hollow segment as shown in FIG. 2b as long as it provides a closing end to the bore of the hollow mount segment.

Figure 3A:
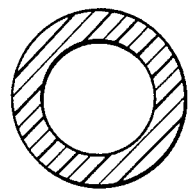
FIG. 3a and 3b are cross-sectional views of the plug taken along lines A—A and B—B in FIG. 2a, respectively.
Figure 3B:
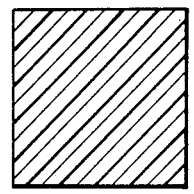

The plug preferably has a cross sectional shape other than a circle on a distal side with respect to the frangible portion 15, the cross section being taken in a direction perpendicular to the longitudinal axis of the plug. FIGS. 3a and 3b are cross sections taken along lines A—A and B—B in FIG. 2a, respectively. More particularly, the first wall portion 9 of the plug 2 with a relative smaller inner diameter which is to be secured to the stepped wall portion 5 of the branch 4 has substantially a true circular cross section having an inner diameter substantially equal to the outer diameter of the stepped wall portion 5 as shown in FIG. 3a. The remaining portion of the plug 2, preferably the closing segment has a non-circular cross section. For example, the closing segment has a square cross section as shown in FIG. 3b. Since the closing segment is a distal segment of the plug which not only closes the bore in the hollow mount segment, but also serves as a handle or lever upon breaking the plug at the frangible portion, the closing segment may have a rectangular, ellipsoidal or other cross section which is convenient to manually grip. Also preferably, the closing segment is an axially elongated segment as shown in FIG. 2b for the same reason.

The tube assembly 1 of the present invention also includes the protector 30 fitted over the plug 2. The protector 30 is in close fit with the outside of the plug 2 for protecting the plug. In the example of FIG. 2a, the protector 30 is a block which defines therein a cavity having an open end and a closed end. An inside portion of the cavity mates with the closing segment of the plug 2. A protector of a modified shape is shown in FIG. 2b. The shape of the protector 30 is not limited to those shown in FIGS. 2a and 2b and the protector may be a tubular sleeve having a portion to be tightly engaged over the closing segment of the plug 2. The protector 30 functions as an ordinary protector for the plug when the branch is not on use, and as a grip when the plug must be broken to render the branch ready for use.

In order that the plug 2 be readily torn off by gripping and twisting the protector 30, the protector 30 preferably has a non-circular outer configuration such as a rectangular, square and ellipsoidal shape.

FIG. 2b shows the components in an assembled state. The plug 2 is mounted on the branch 4 to close its opening 14 and also covered with the protector 30. The first wall portion 9 of the plug is in snug fit over the stepped wall portion 5 of the branch. A space 3 is left between the second wall portion 10 of the plug and the stepped wall portion 5 of the branch in a radial direction. The space 3 is sufficient to keep the open end 6 of the branch 4 from obstructing in breaking the plug 2 at the frangible portion 15. For the same reason, the distal or open end 6 of the branch 4 is axially spaced apart from the plug 2.

The protector 30 must be in snug fit over the plug 2 in order to protect the plug 2 from any accidental external force and to prevent any sliding motion between the protector and the plug when the protector 30 is twisted with a finger grip to tear off the plug 2. The protector is in close fit on the closing segment of the plug 2, but axially extends over the frangible portion 15 with a spacing from the mount segment. A space is left between the inside wall of the protector 30 and the outside wall of the plug 2 at least in a region axially located on the proximal side with respect to the frangible portion 15. In the embodiment shown in FIG. 2b, a space is left between the protector 30 and the mount segment of the plug 2 and the protector 30 is in tight engagement with the closing segment of the plug 2. The space between the inside wall of the protector 30 and the outside wall of the plug 2 bridging over the frangible portion 15 is effective in facilitating separation of the plug 2 by tearing it off.

The fourth opening 14 is closed with the plug 2 covered with the protector 30 when the corresponding branch 4 is not in use. When it is desired to connect another member to the fourth opening 14, the plug 2 is removed from the opening by tearing or twisting off the plug 2 at the frangible portion 15. The branch 4 with its flow path open is now ready for connection to another member.

In the preferred embodiment shown in FIG. 2b, the open end 6 of the branch axially extends beyond the frangible portion 15 of the plug 2 toward the closing segment of the plug. After the plug 2 is removed by gripping the protector 30 and turning the protector so as to tear off the plug 2 at the frangible portion 15, the open end 6 of the branch 4 protrudes beyond the remainder of the plug mount segment left attached to the branch 4. When it is desired to connect another connecting member, for example, a tube having a puncture needle, to the open end 6 of the branch 4, the open end 6 is exposed beyond the plug residue and thus clearly visible to ensure safe connection. There is little likelihood that the other connecting member be inadvertently contacted to the cut edge of the plug 2 which would be sometimes contaminated, thus avoiding contamination of the flow path.

The frangible portion 15 may be formed at any location between the open end 7 and the closed end 8 of the plug. Preferably, the frangible portion 15 is provided in the outside wall of the second or larger inner diameter wall portion 10 of the mount segment of the plug 2. Location of the frangible portion 15 in the second wall portion 10 means that the frangible portion 15 is located radially outside the space 3 between the plug 2 and the branch 4. Then it is very easy to tear off the plug 2 by twisting even though the plug is made of a relatively flexible material.

The engagement between the plug 2 and the protector 30 is not particularly limited as long as it ensures cliping-off of the plug by grasping the protector 30 with fingers and turning it with the plug 2 so as to tear off the plug without any sliding motion between the protector and the plug.

In general, medical tubings are made of polycarbonate and flexible vinyl chloride resin. When a plug is secured to such a tube, it is desired not to use an adhesive at the connection between the plug and the tube in order to avoid contamination to fluid to be passed therethrough, typically blood. If a tube and a plug are made of similar types of material, a blocking bond can be achieved between them by utilizing the heat applied for autoclave sterilization. Since the plug is formed of a relatively flexible material such as polyvinyl chloride resin, it is difficult to tear off the plug with a click by twisting because the plug as a whole is softly twisted. The protector 30 is made of a relatively rigid material in order to facilitate breakage of the plug 2. A choice of the material of the protector 30 is made such that the protector may not be bonded to the branch and the plug through blocking under the influence of the heat applied during autoclave sterilization. A typical examples of the relatively rigid material is a polypropylene resin. A preferred combination of materials meeting the above requirement is a combination of polycarbonate for the branch 4 or tubular body, polyvinyl chloride for the plug 2 and polypropylene for the protector 30. Another preferred combination of materials for the tubular body, plug and protector will occur to those skilled in the art in light of the above teachings.

OPERATION

The operation of the four-way branch tube having a plug mounted on one branch as shown in FIG. 1 is described by referring to a system for plasmapheresis therapy having the branch tube incorporated therein.

As shown in FIG. 4a, the plasmapheresis system includes four sections of tubing connected to the four-way branch tube 1. A first section of tubing extends from a puncture needle 24 placed in the vein of a donor 23 to the first opening 11 of the branch tube for the purpose of blood collection and has a hemostat 28 thereon. A second section of tubing extends from the second opening 12 of the branch tube to a first blood bag 20 and has a hemostat 29 thereon. A third section of tubing extends from the third opening 13 of the branch tube to a second blood bag 21 via a closure member in the form of a click tip 19. A fourth section of tubing extends from the fourth opening 14 of the branch tube to a Y set 22. The fourth section of tubing is a trunk line of the Y set which includes a first inlet line extending to a physiological saline bottle 27 through a clamp 16 and a second inlet line having a clamp 17. This is an outline of the system, and all the lines are not connected at the same time. Connection will become apparent from the following description of operation.

While clamps 16, 17 and 18 on the lines associated with the Y set 22 are closed, a needle connected to the line with clamp 16 is punctured into the saline bottle 27. Then the clamp 16 is opened and the clamp 18 is released to fill the Y set with saline. The clamp 18 is again closed.

During this operation, the plug 2 on the branch 4 of the four-way branch tube is kept normal or unbroken and covered with the protector 30. There is no possibility that the plug is accidentally ruptured to allow contamination of the opening of the branch 4 during manufacture and setting of the branch tube 1. The first opening 11 of the branch tube 1 is in fluid communication with the needle 24, and the second opening 12 in fluid communication with the first blood bag 20. The third opening is connected to the second blood bag 21 although the click tip 19 is also kept normal or unbroken so that the flow path to the second blood bag 21 is closed.

The next step is to connect a connector at the free end of the Y set trunk to the branch 4 of the branch tube. The hemostat 29 is fastened on the second section of tubing connected to the first blood bag 20 in order to prevent reverse flow of medical liquid in the first blood bag 20. Then the plug 2 is torn off at the frangible portion 15 to open the associated branch 4 by manually grasping and twisting the protector 30.

If the plug 2 without the protector 30 is manually twisted, the plug of flexible material tends to be easily deformed and is thus difficult to tear off in a click manner. In contrast, the plug 2 is received in the protector 30 of rigid material such as polypropylene according to the present invention. When the protector 30 is gripped and twisted, the protector in tight engagement over the plug 2 prevents deformation of the plug and assists in tearing off the plug at the frangible portion.

In the preferred embodiment, the open end 6 of the branch 4 extends beyond the frangible portion 15 of the plug 2. After the plug 2 is torn off at the frangible portion 15 by manually twisting the protector 30 along with the plug 2, the open end 6 is exposed and protrudes beyond the torn edge of the plug 2. Then the connector of the Y set 22 is connected to the protruding open end 6 of the branch 4. At this point, the open end 6 of the branch 4 is protruding and visible, connecting operation is very easy and accurate. Contamination is avoided because the connector can be attached to the open end 6 without inadvertent contact with any probably contaminated member.

The next step is to collect blood from the donor 23. The first section of tubing is fastened by the hemostat 28 at a location near the needle 24. The puncture needle is inserted into the vein of the donor 23. After entry of blood into the blood collecting tube is observed, the hemostats 28 and 29 are taken off to communicate an open continuous flow path to the first blood bag 20.

Since the flow path to the second blood bag 21 is closed by the click tip 19 at this point, blood flows under gravity from the needle 24 to the first blood bag 20. Blood collection is continued until the first blood bag 20 is filled with a predetermined volume of blood. Then the section of tubing to the first blood bag 20 is sealed with a tube sealer or a pair of aluminum rings (not shown) and cut therebetween to separate the first blood bag 20.

Figure 4B:
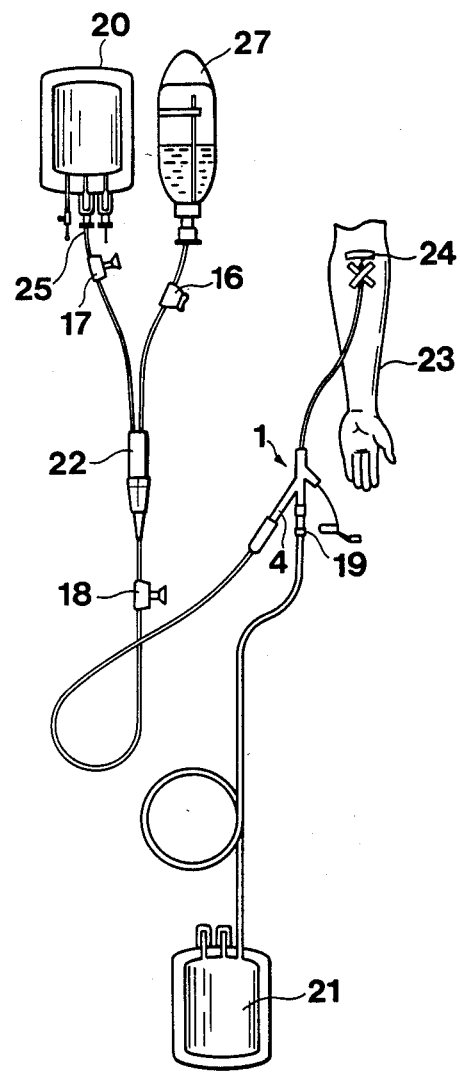

The whole blood in the first blood bag now removed is subjected to centrifugal separation. During the step, saline is transfused dropwise from the bottle 27 to the donor through the Y set 22, the branch 4 with the plug broken, and the needle 24 as shown in FIG. 4b.

The platelet and red cell concentrates thus separated are independently return transfused to the donor 23. More particularly, an outlet 25 of the first blood bag 20 is connected to the second inlet tube of the Y set 22 having the clamp 17. Then the concentrates are returned to the donor 23 through the Y set 22, the four-way branch tube 1, and the needle 24.

At the end of return transfusion, the branch tube 1 is held in one hand, and the click tip 19 is manually torn off to open the flow path to the second blood bag 21. Blood is again collected from the donor 23 to the second blood bag 21 through the needle 24 which has been placed in the vein of the donor. Likewise the first blood bag 20, the blood collected in the second blood bag 21 is centrifugally separated and transfused back to the donor.

In the tube assembly of the present invention, a plug is mounted on one open end of a tubular body or one branch of a branch tube to close the flow path thereof, but breakable and removable from the tubular body to open the flow path. The plug is accommodated in a protector which has a cavity of a shape mating with the plug configuration. The tube assembly has the following benefits.

(1) The plug is protected from any external force applied during manufacture and transportation. Just until the associated tubular body or branch is on use, there is little possibility that the plug is accidentally ruptured to cause contamination of the flow path of the tubular body.

(2) The open end of the tubular body or branch closed with the plug can be opened with the protector fitted over the plug, eliminating the risk of contamination of the open end which is detrimental when the branch is used as a cell return inlet.

(3) Since the protector is fitted over the plug, the area available for gripping is increased as compared with the plug without the protector, facilitating tearing-off operation to open the flow path.

(4) In the embodiment wherein the open end of the tubular body or branch extends beyond the frangible portion in the plug toward the closing end thereof, another member can be readily connected to the open end after the plug is torn off at the frangible portion, avoiding the risk of contaminating the flow path of the branch.

(5) In the embodiment wherein the frangible portion is formed in the outside wall of the second wall portion of the plug having a relatively larger inner diameter, it is easy to tear off the plug at the frangible portion even though the plug is made of flexible material.

(6) In the embodiment wherein the closing segment of the plug and the corresponding portion of the protector have a non-circular cross section, the protector is easy to grip for breakage.

We claim:

1. A tube assembly comprising
   a tubular body having at least two open ends,
   a plug of a relatively flexible material mounted on one open end of said tubular body, said plug including
   (a) a hollow mount segment having an open end, a portion of the mount segment extending from its open end being fixedly secured to the one open end of said tubular body,
   (b) a closing segment axially connected to the mount segment, and
   (c) a frangible portion located axially outside the secured portion whereby said plug is breakable at the frangible portion and removable from the one open end of the tubular body, and
   means comprised of a relatively rigid material fitted over the closing segment of the plug and extending over the frangible portion of the plug for protecting the frangible portion of the plug and for gripping the plug in order to break in the plug along the frangible portion tube assembly ready for use.

2. The tube assembly of claim 1 wherein said protecting and gripping means has such a hardness that it will not prevent breakage of the plug at the frangible portion.

3. The tube assembly of claim 1 wherein the closing segment of said plug has a non-circular cross section.

4. A tube assembly comprising
   a tubular body having at least two open ends,
   a plug of a relatively flexible material mounted on one open end of said tubular body, said plug including
   (a) a hollow mount segment having an open end, a portion of the mount segment extending from its open end being fixedly secured to the one open end of said tubular body, and including a first wall portion with a relatively smaller inner diameter extending from the open end of the mount segment being secured to the one open end of said tubular body and a second wall portion with a relatively larger inner diameter extending from the first wall portion to the closing segment,
   (b) a closing segment axially connected to the mount segment, and
   (c) a frangible portion located axially outside the secured portion and having a circumferential notch in the outer surface of said second wall portion whereby said plug is breakable at the frangible portion and removable from the one open end of the plug, and
   a protective cover of a relatively rigid material fitted over the plug.

5. A tube assembly comprising
   a tubular body having at least two open ends,
   a plug of a relatively flexible material mounted on one open end of said tubular body, said plug including
   (a) a hollow mount segment having an open end, a portion of the mount segment extending from its open end being fixedly secured to the one open end of said tubular body,
   (b) a closing segment axially connected to the mount segment, and
   (c) a frangible portion located axially outside the secured portion whereby said plug is breakable at the frangible portion and removable from the one open end of the tubular body, and a protective cover of a relatively rigid material fitted over the plug wherein said protective cover is in close fit on the closing segment of said plug, but extends over the frangible portion with a spacing from the mouth segment.

6. A tube assembly comprising a tubular body having at least two open ends, a plug of a relatively flexible material mounted on one open end of said tubular body, said plug including (a) a hollow mount segment having an open end, a portion of the mount segment extending from its open end being fixedly secured to the one open end of said tubular body, (b) a closing segment axially connected to the mount segment, and (c) a frangible portion located axially outside the secured portion whereby said plug is breakable at the frangible portion and removable from the one open end of the tubular body, and a protective cover of a relatively rigid material fitted over the plug, wherein said open end of said tubular body axially extends beyond the frangible portion of said plug toward the closing segment of said plug.

* * * * *